United States Patent [19]

Adams

[11] Patent Number: 5,246,009
[45] Date of Patent: Sep. 21, 1993

[54] GUIDE WIRE ASSEMBLY AND METHOD FOR CATHETER EXCHANGE

[75] Inventor: Daniel O. Adams, Blaine, Minn.

[73] Assignee: SciMed Life Systems, Inc., Maple Grove, Minn.

[21] Appl. No.: 763,363

[22] Filed: Sep. 20, 1991

[51] Int. Cl.⁵ .............................................. A61B 5/00
[52] U.S. Cl. ................................... 128/772; 128/657; 604/283
[58] Field of Search .................. 128/657, 772; 604/95, 604/164, 283

[56] References Cited

U.S. PATENT DOCUMENTS

| | | | |
|---|---|---|---|
| 4,820,288 | 4/1989 | Isono | 604/283 |
| 4,875,489 | 10/1989 | Messner et al. | 128/657 |
| 4,878,900 | 11/1989 | Sundt | 604/283 |
| 4,922,924 | 5/1990 | Gambale et al. | 128/772 |
| 5,109,867 | 5/1992 | Twyford | 128/772 |
| 5,113,872 | 5/1992 | Jahrmarkt et al. | 128/772 |

*Primary Examiner*—Max Hindenburg
*Attorney, Agent, or Firm*—Kinney & Lange

[57] ABSTRACT

A guide wire assembly includes an inner core wire and an outer tube. The inner core wire has a proximal end, a distal end and a torque transmission portion and the outer tube includes a proximal end and a distal end. The distal end of the outer tube is coaxially mountable over the proximal end of the inner core wire and extendable distally on the inner core wire to the torque transmission portion. The torque transmission portion defines a raised taper which is frictionally engageable by a recessed taper within the distal end of the outer tube to releasably couple the outer tube to the inner core wire for torque transmission therebetween.

28 Claims, 4 Drawing Sheets

GUIDE WIRE ASSEMBLY AND METHOD FOR CATHETER EXCHANGE

BACKGROUND OF THE INVENTION

The present invention relates to the field of angioplasty. In particular, the present invention is a two-piece guide wire assembly usable with a coaxially mountable dilatation balloon catheter.

Angioplasty has gained wide acceptance in recent years as an efficient and effective method for treating types of vascular diseases. In particular, angioplasty is widely used for opening stenosis in the coronary arteries, although it is also used for treatment of stenosis in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. Inflation of the balloon causes stretching of the artery and pressing of the lesion into the artery wall to re-establish acceptable blood flow through the artery.

Over-the-wire catheters and fixed wire (i.e., non-over-the-wire) catheters are two types of dilatation catheters that are commonly used in angioplasty. An over-the-wire catheter has an inflation lumen and a guide wire through lumen through which a guide wire is advanced to establish a path through the stenosis. The separate dilatation catheter is then advanced over the guide wire until the balloon is positioned across the stenosis. The lumen for the guide wire must be sized with an inside diameter larger than the guide wire for easy wire movement. A fixed wire catheter has its own built in guide wire such that the guide wire, balloon and inflation lumen comprise a single unit.

Profile is a term used to designate the smallest opening a deflated, folded balloon of a dilatation catheter can traverse without damage to the catheter. Due to their "single unit" construction and no guide wire through lumen, fixed wire catheters generally have the advantage of having a smaller profile than over-the-wire catheters allowing fixed wire catheters to traverse smaller stenosis than over-the-wire catheters. However, separate guide wires as used with over-the-wire catheters are considered to be more steerable than fixed wire catheters due to being small in diameter.

Sometimes during the installation of a dilatation catheter (either over-the-wire or fixed wire), the balloon profile of the dilatation catheter is too large to cross the stenosis or the balloon inflated diameter is so small that the balloon cannot effectively dilate the stenosis. In other cases, the dilatation catheter may lack the control or flexibility necessary to track a path to the stenosis. In either situation, the catheter must be exchanged for one with a different size balloon or for one with different tracking characteristics to alleviate the respective difficulty.

To exchange an over-the-wire catheter, the guide wire must first be replaced by one 300 cm. long or the normal 175 cm. wire extended to 300 cm. by adding an extension wire to the proximal end of the guide wire located outside the patient's body. A typical balloon catheter is 135 cm. long. The dilatation catheter is then removed from the guide wire by holding the proximal end of the extended guide wire in place while pulling back on the catheter until the catheter is outside of the patient's body. By similar means a different catheter is placed on the guide wire and advanced to the area of the stenosis. The guide wire remains in position within the vascular system during the exchange of catheters such that the path to the stenosis need not be re-established. Not having to recross the lesion with a guide wire reduces the possibility of entering a false lumen.

To exchange a fixed wire catheter, the catheter within the patient's vascular system is removed and a different catheter is inserted in its place. This exchange of catheters necessarily requires removal of the built in guide wire portion of the catheter from the stenosis due to the "single unit" construction of the catheter and guide wire. Thus, to advance a fixed wire catheter to a stenosed area, the entire pathway through the vascular system must be re-established since no portion of the fixed wire catheter remains within the vascular system during the exchange. Establishing a path through the arterial tree to a stenosis is a difficult procedure and there is the potential of entering a false lumen. Thus, having to accomplish this task more than once is undesirable.

The profile of a dilatation catheter (either over-the-wire or fixed wire) dictates the minimum size of stenoses that are traversable by the catheter. The torqueability of a guide wire (whether separate or built in) determines the control necessary to maneuver and steer the guide wire or fixed wire catheter through the tortuous arterial paths within the vascular system. Both the guide wire and the fixed wire catheter have a distal spring tip that is formed in a bend such that torque applied to the proximal end of the guide wire or the fixed wire catheter is transmitted to the distal end for steering through the arterial branch vessels.

In the case of an over-the-wire catheter, if the diameter of the guide wire is below a nominal level, torque applied to the proximal end of the guide wire will only be partially transmitted through the length of the guide wire shaft to its distal end. This ineffective torque transmission results in a inability to adequately control the angular position of the guide wire distal tip. Thus, the nominal diameter of a guide wire shaft is partially determined by the requirement of being able to effectively transmit torque throughout the entire length of the guide wire shaft. For example, a 0.018" diameter guide wire is considered to be more torqueable than a 0.014" diameter guide wire.

In order to have the convenience of an over-the-wire catheter system and the lowest profiles, many over-the-wire catheter manufacturers have reduced the diameter of the guide wire through lumen so that only 0.014" diameter or smaller guide wires can be used. The guide wire lumen inside diameter is typically about 0.002" to 0.003" larger than the guide wire to allow for exchangeability and free wire movement of the catheter over the guide wire. Therefore, an over-the-wire catheter that is useable with a 0.014" diameter guide wire has a lower profile when compared to a similar catheter designed for use with a 0.018" diameter guide wire. However, the 0.014" diameter guide wire has the disadvantage of reduced guide wire torque control due to its smaller guide wire diameter when compared to the 0.018" diameter guide wire.

It is evident that there is a continuing need for improved over-the-wire catheter systems. In particular, there is a need for a catheter system that permits a reduction in the profile of over-the-wire dilatation catheters without sacrificing the guide wire torque control or torqueability level found in 0.018" or larger diameter guide wires. In addition, the catheter system should allow dilatation catheter exchangeability over the guide wire system.

SUMMARY OF THE INVENTION

The present invention is a guide wire assembly that includes an inner core wire and an outer tube. The inner core wire has a proximal end, a distal end, and a torque transmission portion between the distal end and the proximal end. The outer tube includes a proximal end and a distal end that is co-axially mountable over the proximal end of the inner core wire so that the proximal end of the outer tube is disposed distally of the proximal end of the inner core wire. The outer tube is extendable over the inner core wire up to the torque transmission portion, where a recessed taper of the outer tube is engageable with a raised taper defined by the torque transmission portion of the inner core wire. Cooperation between the raised and recessed tapers releasably couples the distal end of the outer tube to the torque transmission portion of the inner core wire allowing torque transmission between the outer tube and the inner core wire.

In one embodiment of the present invention, the inner core wire has a constant diameter from its proximal end to the torque transmission portion, and an overall length greater than twice the length of the outer tube or approximately 300 cm. The torque transmission portion of the inner core wire has a diameter that increases distally to a maximum diameter of the inner core wire, thereby forming the raised taper. This maximum diameter is smaller than the outside diameter of the outer tube. The distal portion of the inner core wire has a diameter that decreases distally from the maximum diameter of the inner core wire to a minimum diameter at the distal end of the core wire to provide increased flexibility for traversing tortuous vessels. The outer tube has a core wire through lumen which has a constant diameter from the proximal end of the outer tube to a point just proximal of the distal end of the outer tube, and then the core wire through lumen diameter increases distally to the distal end thereby forming the recessed taper.

To engage the outer tube recessed taper to the inner core wire raised taper, one simply applies a force on the outer tube moving it distally relative to the inner core wire while holding the inner core wire with a proximally applied force. To release the tapers the process is reversed. That is, a distally directed force on the inner core wire and a simultaneous proximally directed force on the outer tube causes the two tapers to separate and uncouple.

Alternatively, the outer tube may be releasably coupled to the inner core wire for torque transmission by way of snap-fit coupler. The snap fit coupler includes a plurality of ribs formed on the inner wall of the distal end of the outer tube. These ribs are configured to engage a plurality of grooves formed in a proximal end of the distal portion of the inner core wire. The inner wall of the outer tube further includes a concentric ridge which is adapted to engage a concentric channel formed in the inner core wire for releasably securing the outer tube to the core wire. Interengagement of the ribs and grooves allows torque to be transmitted from the outer tube to the distal portion of the inner core wire.

In one embodiment, a radiopaque spring tip is affixed on the distal end of the inner core wire and a separate shaping ribbon extends between and connects a distal end of the spring tip to the distal end of the inner core wire. In addition, a torque sleeve is mounted on the proximal end of the outer tube.

In an alternative embodiment, the shaping ribbon is formed integrally with the inner core wire.

A method of exchanging a first over-the-wire catheter in a patient's vascular system for a second over-the-wire catheter includes a first step of providing a guide wire assembly over which the first over-the-wire catheter is mounted, wherein the guide wire assembly has an inner core wire and an outer tube co-axially movably mounted over the inner wire. Next, a proximal portion of the inner wire is held outside of the vascular system to maintain the position of the inner core wire within the vascular system. The outer tube and the first over-the-wire catheter are then moved proximally relative to the inner core wire to release the taper lock as previously described and are then withdrawn out of the vascular system to expose a portion of the inner core wire distally from the outer tube and the first over-the-wire catheter. The inner core wire is held at this exposed portion to maintain the position of the inner core wire within the vascular system and then the simultaneously held proximal portion of the inner core wire is released. Next, the first over-the-wire catheter and the outer tube are withdrawn from the proximal end of the inner core wire and the outer tube is then removed from within the first over-the-wire catheter.

Next, a distal end of the outer tube is installed within the proximal end of a second over-the-wire catheter guide wire lumen, and then the distal end of the second over-the-wire catheter and outer tube are installed onto the proximal end of the inner core wire and moved distally to the exposed portion of the inner core wire. Again, the proximal portion of the inner core wire is held outside of the vascular system to maintain the position of the core wire within the vascular system and the simultaneously held exposed portion of the core wire is released. Finally, the outer tube and the second over-the-wire catheter are further moved distally over the inner core wire to establish the second over-the-wire catheter in a desired position within the vascular system.

The method of catheter exchange may also include additional steps. One such additional step is advancing the outer tube in the second over-the-wire catheter distally over the inner core wire to a point in which the outer tube and the inner wire taper lock to allow torque transmission therebetween, thereby limiting relative movement between the inner and outer tubes.

The guide wire assembly of the present invention substantially reduces the distal profile of guide wire shafts which allows a reduction in the profile of cooperating exchangeable over-the-wire dilatation catheters. The guide wire assembly also does not suffer a loss of control or torqueability that normally occurs when reducing the proximal profile of a typical guide wire to achieve the advantage of use of an exchangeable lower profile catheter. Furthermore, this reduction in catheter profile allows stenoses having smaller openings to be crossed than were previously traversable with typical larger diameter guide wires. Thus, a greater range of sizes of stenosed arteries can be crossed by dilatation catheters using the guide assembly of the present invention. In addition, this guide wire assembly allows catheters to be exchanged without sacrificing the previously established path through the vascular system to the stenosed area.

While the above identified drawing figures set forth a preferred embodiment, other embodiments of the present invention are also contemplated, as noted in the discussion. In all cases, this disclosure presents illustrated embodiments of the present invention by way of representation and not limitation. It should be understood that numerous other modifications and embodiments can be devised by those skilled in the art which fall within the scope and spirit of the principles of this invention. It should be noted that the figures have not been drawn to scale as it has been necessary to enlarge certain portions for clarity. In addition, the use of such relational terms as left/right, upper/lower, horizontal/vertical, etc. are used herein for reference purposes only and are not intended to be limiting features of the invention disclosed.

DETAILED DESCRIPTION OF THE PREFERRED EMBODIMENTS

Figure 1:
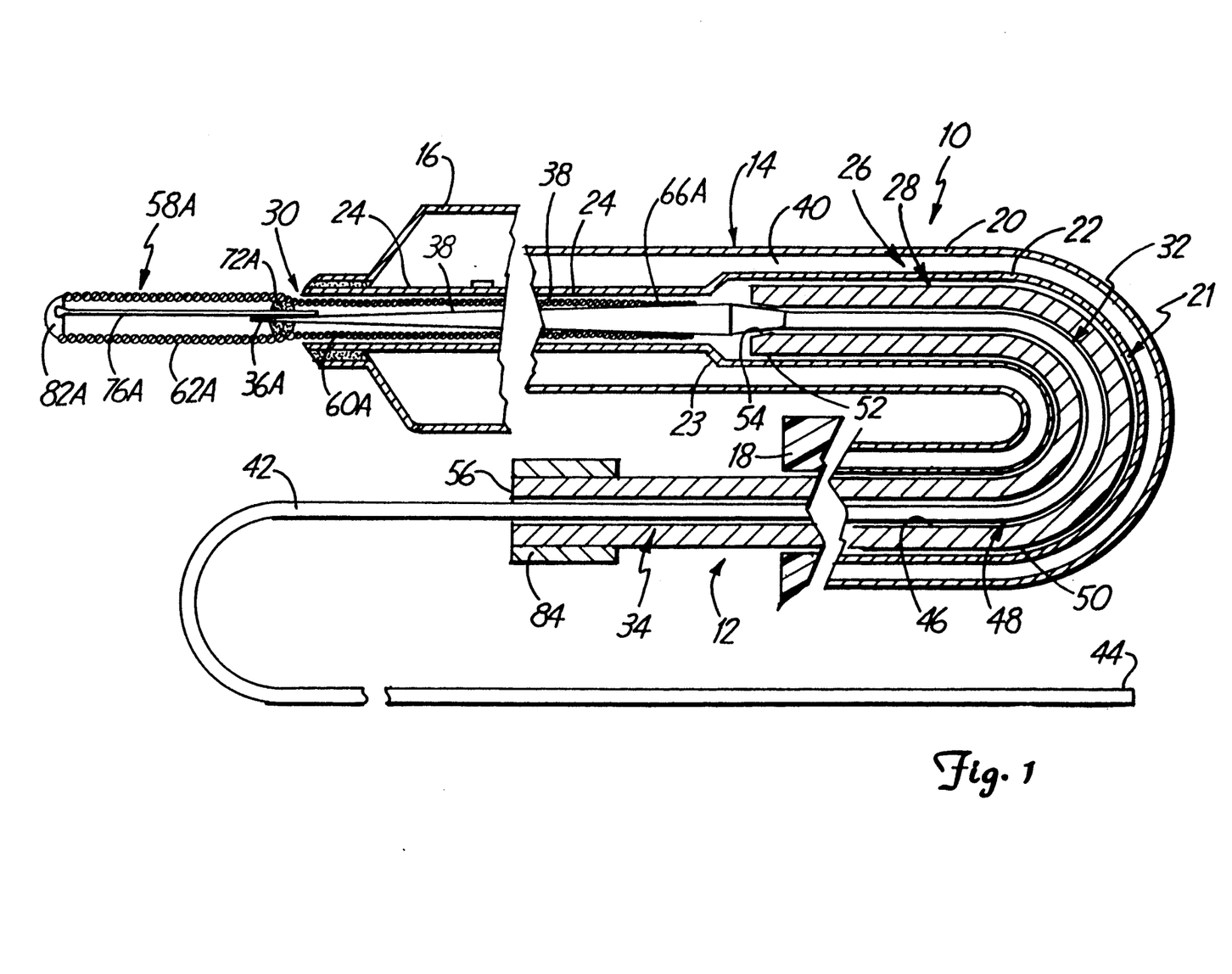
FIG. 1 is an elevational view of an over-the-wire catheter with a guide wire assembly in accordance with the present invention situated therein.

An over-the-wire catheter 10 which includes a guide wire assembly 12 in accordance with the present invention is illustrated generally in FIG. 1. The guide wire assembly 12 is better illustrated in FIGS. 2-7 and is described in detail in subsequent portions of the specification. However, a complete understanding of the guide wire assembly 12 will be facilitated by the following general description of the over-the-wire catheter 10.

As seen in FIG. 1, over-the-wire catheter 10 includes a multi-lumen shaft 14 which has an inflatable balloon 16 mounted at its distal end and a conventional manifold 18 mounted at its proximal end. The shaft 14 includes an outer tube 20 and an inner tube 21 (formed by a proximal inner tube section 22, a necked down portion 23 and a distal inner tube section 24). The diameter of the proximal inner tube section 22 is greater than the diameter of the distal inner tube section 24 because added stiffness at the proximal end of the catheter 10 is desired for reasons of pushability and torqueability. The reduced diameter of the distal inner tube section 24 results in added flexibility at the distal end of the catheter 10 for trackability through tortuous arterial vessels.

An inflation lumen 26 is defined between the outer walls of the inner tube sections 22 and 24 and the inner wall of outer tube 20. The inflation lumen 26 extends from an inlet port (not shown) of the manifold 18 to the interior of the balloon 14. A guide wire through lumen 28 extends through the interior of the inner tube sections 22 and 24 from the manifold 18 to a distal opening 30 at the distal end of the catheter 10, for reception of the guide wire assembly 12. The guide wire assembly 12 extends proximally through the manifold 18.

Figure 2:
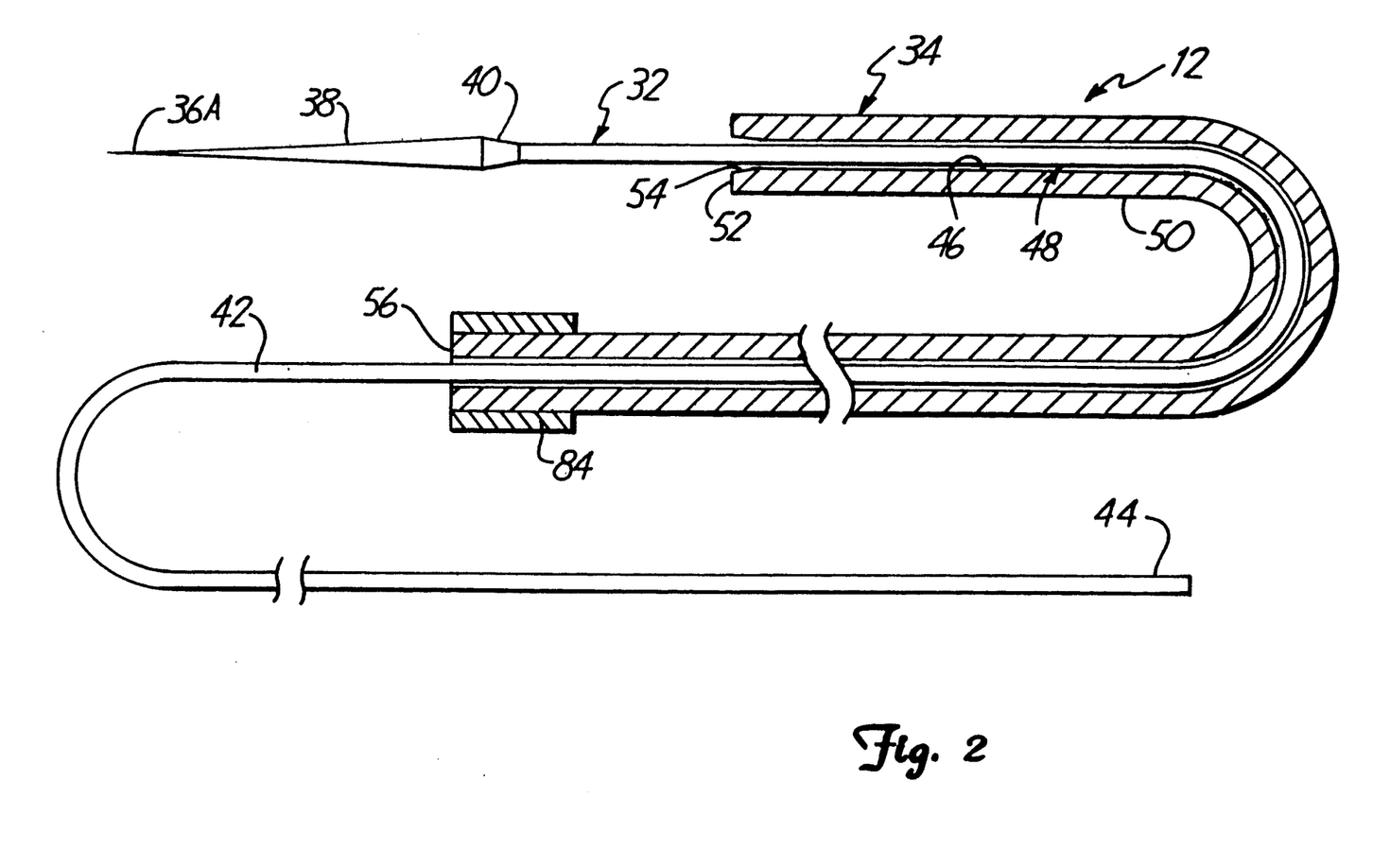
FIG. 2 is an elevational view partially in section of the guide wire assembly of the present invention with its radiopaque spring tip removed therefrom for clarity.

As seen in FIG. 2, the guide wire assembly 12 includes an inner core wire 32 and an outer tube 34, both of which are preferably made from stainless steel. The inner core wire 32 has a distal end 36A, a distal portion 38 and a torque transmission portion defined by a raised taper 40 which is located proximally of distal portion 38. A proximal portion 42 of inner core wire 32 extends from the raised taper 40 to a proximal end 44 of the inner core wire 32. The raised taper 40 preferably has a linearly varying diameter. The raised taper 40 has a maximum diameter of 0.012" adjacent the proximal end of distal portion 38, the diameter decreasing proximally until it reaches a minimum diameter of 0.005/0.006" adjacent a distal end of proximal portion 42. The proximal portion 42 from the raised taper 40 to the proximal end 44 of inner core wire 32 has a constant diameter of 0.005/0.006".

As seen in FIG. 2, the outer tube 34 has an inner wall 46 defining a inner core wire through lumen 48 and an outer wall 50. The outer tube 34 is coaxially mountable on and longitudinally slidable over the inner core wire 32 by way of the core wire through lumen 48. The outer tube 34 extends from a distal end 52, which has a recessed taper 54, to a proximal end 56. The distal end 52 is mountable over the proximal end 44 of inner core wire 32 such that the proximal end 56 of the outer tube 34 is disposed distally of the proximal end 44 of the inner core wire 32.

The recessed taper 54 has a minimum diameter of 0.007/0.008" at a distal end of the core wire through lumen 48 and increases distally with a linear taper that matches the taper of the raised taper 40 of the inner core wire 32. The core wire through lumen 48 has a constant diameter of 0.007/0.008" from the proximal end 56 of the outer tube 34 to a proximal end of the recessed taper 54. The outer diameter of the outer tube 34 is in the range of 0.014" to 0.020". The exact dimension within this range is dependent upon and must be less than the inside diameter of the proximal inner tube section 22 of the catheter 10. The outer tube 34 is approximately 110 to 115 cm. in length as measured from its proximal end 56 to its distal end 52.

Figures 3, 4:
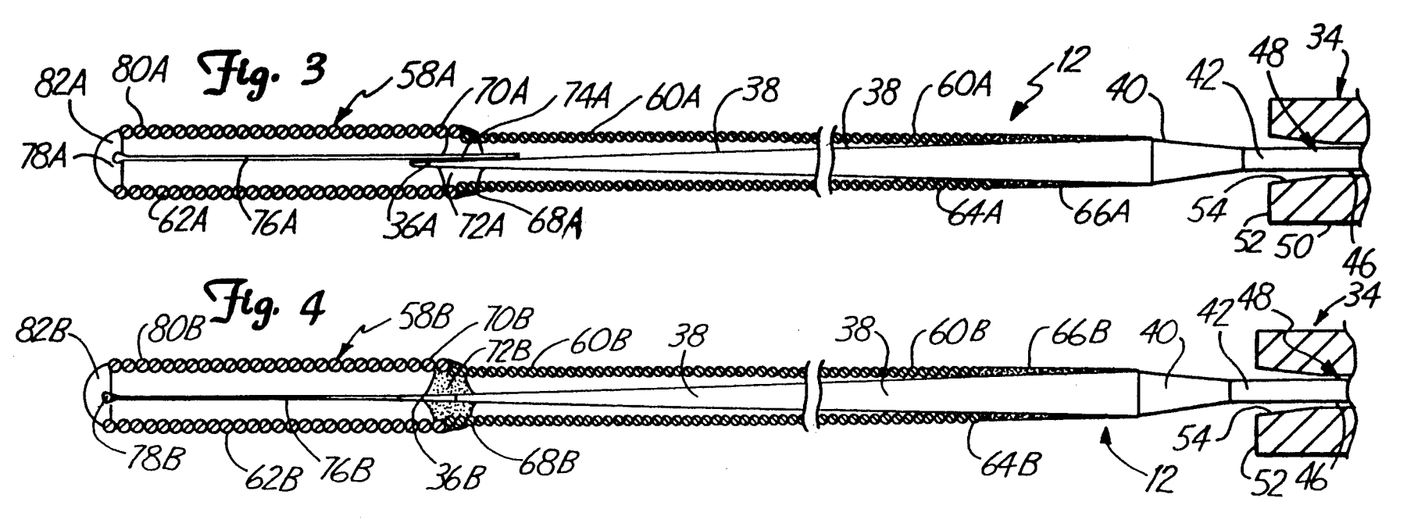
FIG. 3 is an enlarged fragmentary view partially in section showing particulars of a spring tip construction of the guide wire assembly of the present invention.
FIG. 4 is an enlarged fragmentary view partially in section showing particulars of an alternative spring tip construction of the guide wire assembly of the present invention.

As seen best in FIG. 3, the inner core wire 32 includes a radiopaque spring tip 58A to facilitate maneuvering of the inner core wire 32 through the vascular system of a patient. The radiopaque spring tip 58A includes a proximal spring coil segment 60A and a distal spring coil segment 62A. A proximal end 64A of the proximal spring coil segment 60A is secured to the distal portion 38 of the inner core wire 32 by way of a braze or solder joint 66A. A distal end 68A of the proximal spring coil segment 60A and a proximal end 70A of the distal spring coil segment 62A are secured to one another and to the distal end 36A of the inner core wire 32 via a braze or solder connection 72A. The connection 72A further secures a proximal end 74A of a separate shaping ribbon 76A to the distal end 36A of the inner core wire 32. The shaping ribbon 76A extends distally from the inner core wire 32 and a distal end 78A of the shaping ribbon 76A is secured to a distal end 80A of the distal spring coil segment 62A via a distal tip weld 82A. The shaping ribbon 76A can be bent to a desired shape to assist steering of the guide wire assembly 12 through the vascular system of a patient.

The radiopaque spring tip 58A is used to provide non-traumatic maneuvering and kink resistance to the inner core wire 32 as it is steered through the vascular system. The proximal and distal spring coil segments 60A and 62A are made of a radiopaque material which is observable using x-ray fluoroscopy to monitor the position of the spring tip 58A of inner core wire 32 within the vascular system and guide catheter. The distal spring coil segment 62A of inner core wire 32 adds strength, kink resistance and a smooth constant diameter to the distal portion 38 thereby improving control of the inner core wire 32 during maneuvering of the inner core wire 32 within the vascular system.

The proximal and distal spring coil segments 60A and 62A are preferably made of a radiopaque platinum alloy wire of 0.002" to 0.003" diameter material. The distal spring coil segment 62A is approximately one centimeter to three centimeters in length and has an outer diameter ranging from 0.012–0.018 inches. The proximal spring coil segment 60A may vary in length and has roughly the same diameter as the maximum diameter of the inner core wire 32 at the raised taper 40 or typically 0.012". The shaping ribbon 76A may also be made of stainless steel wire of 0.002"×0.004".

An alternative spring tip 58B is shown in FIG. 4, wherein the shaping ribbon 76B is formed integrally with the distal end 36B of the inner core wire 32. In this embodiment the connection 72B merely secures the distal end 68B of the proximal spring coil segment 60B and the proximal end 70B of the distal spring coil segment 62B to the distal end 36B of the inner core wire 32. Alternatively, spring coil segments 60A, 62A and 60B, 62B could be fabricated as a single element of continuous wire. In FIG. 4 in this mode, connection 72B may not be needed. In FIG. 3 in this mode, connection 72A may only be needed to connect the proximal end 74A of the shaping ribbon 76A to the distal end 36A of the inner core wire 32.

The inner core wire 32 is capable of being inserted into and steered through the tortuous paths of the arterial tree. The spring tip 58A of the inner core wire 32 is insertable into a guide catheter (not shown) and acts as the leading tip of the inner core wire 32 as it negotiates the path through the vascular system and across the stenosis. Distal portion 38 of the inner core wire 32 has a tapered diameter which increases proximally from the distal end 36A to the maximum diameter of inner core wire 32 (i.e., 0.012") at the raised taper 40. The distal portion 38 of inner core wire 32 is approximately 10% of the total length of the inner core wire 32 or typically for coronary use 30 cm. to 38 cm. in length. The inner core wire 32 is approximately 300 cm. in length when measured from its proximal end 44 to its distal end 36A. The length of the inner core wire 32 from its proximal end 44 to the distal end of the raised taper 40 is approximately 262 cm. to 270 cm. The diameter of the distal portion 38 in the alternative embodiment reduces to the 0.002"× 0.004" shaping ribbon 76B since the shaping ribbon 76B is formed integrally with the inner core wire 32.

The tapered diameter of distal portion 38 of the inner core wire 32 allows for increased flexibility and maneuverability of the inner core wire 32 when negotiating a path through the vascular system. The low profile of distal portion 38 also allows the use of lower profile dilatation catheters since the distal inner diameter of the catheters may be substantially reduced when used with a low profile inner core wire 32 as described.

Figure 5:
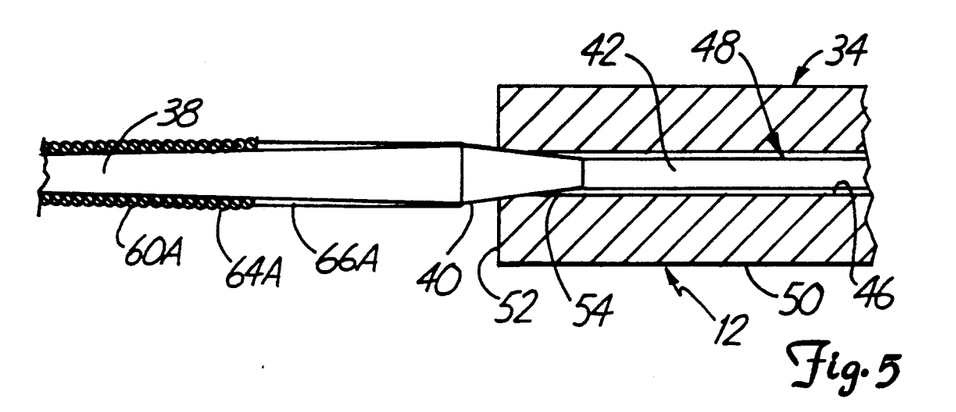
FIG. 5 is a greatly enlarged fragmentary view partially in section of the guide wire assembly of the present invention showing an inner core wire releasably coupled to an outer tube.

As seen in FIG. 5, interengagement between the raised taper 40 and recessed taper 54 releasably couples the outer tube 34 to the inner core wire 32. The raised taper 40 of the inner core wire 32 prevents distal movement of the outer tube 34 beyond the raised taper 40. To couple the inner core wire 32 to the outer tube 34, the distal end 52 of outer tube 34 is moved distally over the core wire 32 until it is adjacent the raised taper 40. The distal end 52 is then pushed distally until the surface of recessed taper 54 contacts the surface of raised taper 40. The surfaces frictionally engage due to pressure exerted from urging of the recessed taper 54 distally against the raised taper 40.

Once the raised taper 40 has been coupled to the recessed taper 54 (see FIG. 5), the outer tube 34 may be rotated to cause rotation of the inner core wire 32. The outer tube 34 is rotated by torque applied to the proximal end 56 of outer tube 34 wherein the torque is transmitted through the shaft of outer tube 34 to its distal end 52. The torque present at distal end 52 of outer tube 34 is transmitted to the inner core wire 32 through the coupled raised taper 40 and recessed taper 54, thereby causing rotation of the inner core wire 32. In particular, the distal portion 38 of inner core wire 32 is selectively rotated to manipulate the guide wire assembly 12 within the vascular system as desired. The mated tapers 40 and 54 may be disengaged by pulling the outer tube 34 proximally over the inner core wire 32 to decouple the core wire 32 and outer tube 34 from the torque transmitting state.

An optional torque sleeve 84 is mounted upon the proximal end 56 of the outer tube 34 to facilitate the application of torque to the outer tube 34 and the inner core wire 32. The torque sleeve 84 is preferably coaxially slidable over the proximal end 56 of the outer tube 34 and has an outer diameter (i.e., 0.25"×0.50") appreciably greater than the outer diameter of the outer tube 34, so that the user-applied torque is enhanced.

Preferably, a lubricous coating is applied to the inner core wire 32 and the inner and outer surfaces of the outer tube 34. The coating reduces friction between the coaxially slidable components to facilitate their interaction. The lubricous coating may be a polytetrafluoroethylene coating on the outside diameter or silicone based coating on the inside diameter of outer tube 34.

To install the guide wire assembly 12 and a the over-the-wire dilatation catheter 10 within a stenosed coronary artery, a guide catheter is first provided within the vascular system. The distal end of the guide catheter is inserted into the femoral artery located in the thigh and pushed distally up through the vascular system until the distal end of the guide catheter is located in the ostium of the coronary artery. The proximal end of the guide catheter protrudes outside of the body and vascular system at the femoral artery to provide an entry way for subsequent insertion of additional angioplasty devices. Thus, the guide catheter establishes a pathway from outside the body (at the thigh) to the ostium of the coronary artery adjacent the stenosed area.

Next, the over-the-wire dilatation catheter 10 and the guide wire assembly 12 of the present invention are prepared for insertion within the guide catheter. The distal end 52 of the outer tube 34 is inserted within the proximal end of the catheter guide wire through lumen 28 and pushed distally into the catheter. Next, the distal end of the catheter guide wire through lumen 28 is installed over the proximal end 44 of the inner core wire 32. The catheter 10 is then moved distally over the inner core wire 32 such that the core wire 32 passes through the core wire lumen 46 of the outer tube 34. Distal movement of the catheter 10 ceases when the outer tube 34 is adjacent to the distal portion 38 of the core wire 32 and the catheter distal tip is adjacent the distal end 36A of the core wire 32. The assembled combination of inner core wire 32, outer tube 34, and catheter 10 are then inserted within the proximal end of the guide catheter. The spring tip 58A of the inner core wire 32 protrudes out of the distal end of the catheter 10 and is used to initiate a path through the guide catheter and vascular system. A bend of the distal spring coil segment 62A and the shaping ribbon 76A facilitates steering into various branches of the vascular system.

Before the assembled combination is moved further within the guide catheter, the outer tube 34 is further advanced distally over the inner core wire 32 until the recessed taper 54 of the outer tube 34 mates with the raised taper 40 of the inner core wire 32. Once the outer tube 34 and the core wire 32 are coupled together, further distal movement of outer tube 34 relative to the inner core wire 32 is limited and any torque applied to the outer tube 34 is transmitted to the inner core wire 32. Torque transmitted to the inner core wire 32 is used to steer or control the distal portion 38 of the inner core wire 32 within the guide catheter and vascular system.

The assembled combination is then pushed distally up through the guide catheter and vascular system until the distal end 36A of inner core wire 32 and the distal end of the catheter 10 are adjacent the distal end of the guide catheter. Thereafter, the distal end 36A of the inner core wire 32 and the distal end of the catheter 10 are pushed out of the distal end of the guide catheter and through the ostium of the coronary artery and maneuvered through the arterial branches until the distal end 36A of the core wire 32 has crossed the lesion and the balloon 16 of the over-the-wire catheter 10 is centered in the stenosis.

Upon a complete and successful positioning of the catheter balloon 16 within the stenosis, the balloon 16 is inflated to open the stenosed area. Dilatation of the stenosed area can be repeated at various pressures until an acceptable reduction in the stenosis is achieved and blood flow through the stenosed area is improved.

Sometimes the previously described catheter dilatation procedure is hampered by the catheter having poor tracking or profile characteristics such that the installation procedure cannot be completed. In other instances, after a successful installation, the balloon profile is too large to fit through the stenosis or the inflated balloon so small that the stenosis cannot be adequately dilatated. When this difficulty occurs, the catheter must be backed off the guide wire out of the vascular system and exchanged for one having different tracking, profile or balloon size characteristics.

To exchange dilatation catheters, a unique method of exchanging a first over-the-wire balloon catheter in a vascular system for a second over-the-wire balloon catheter is used. After the guide wire assembly 12 and the first over-the-wire catheter have been provided within the guide catheter and vascular system by the previously described installation procedure, the distal portion 38 of the inner core wire 32 is held in position across the stenosis by grasping the proximal portion 42 of the inner core wire 32 from outside of the vascular system near the proximal end 56 of the outer tube 34.

Next, the proximal end 56 of the outer tube 34 and the first over-the-wire catheter are grasped and pulled proximally over the inner core wire 32 and withdrawn out of the guide catheter until a portion of inner core wire 32 extending proximally out from the proximal end of the guide catheter is exposed distally from a distal end of the first catheter. During this procedure the grasping position of proximal portion 42 must be repositioned more proximally after each small proximal movement of the outer tube 34 relative to core wire 32. The inner core wire 32 is then grasped at this exposed portion to ensure that the distal portion 38 of inner core wire 32 remains across the stenosis. Thereafter, the proximal portion 42 of the inner core wire 32 being held outside of the vascular system is released. Finally, the first over-the-wire catheter and outer tube 34 are fully withdrawn from the inner core wire 32 so that outer tube 34 and the catheter are fully removed from within the vascular system.

Once the outer tube 34 and the first over-the-wire catheter are removed from the core wire 32, the proximal end 56 of the outer tube 34 is grasped and pulled proximally relative to the dilatation catheter to remove the outer tube 34 from the first over-the-wire catheter guide wire through lumen. The distal end 52 of the outer tube 34 is then installed into a proximal end of a second over-the-wire catheter. The exposed portion of the inner core wire 32 located proximally to the proximal end of the guide catheter is held, and the outer tube 34 and second catheter are then moved distally over the inner core wire 32 until the distal end of the second catheter is adjacent the exposed portion of the core wire 32 near the proximal end of the guide catheter. Again, the proximal portion 42 of the inner core wire 32 is held outside of the vascular system to maintain the position of the core wire 32 across the stenosis and the exposed portion of the core wire 32 is released. Finally, the outer tube 34 and second over-the-wire catheter are further moved distally over the core wire 32 to establish the second over-the-wire catheter in a desired position within the vascular system.

Additional steps of the catheter exchange method may be performed to further maneuver the guide wire assembly 12 and second over-the-wire catheter within the vascular system. In a first additional step, the outer tube 34 and second over-the-wire catheter are further advanced distally over the proximal portion 42 of the inner core wire 32 until the distal end 52 of the outer tube 34 is adjacent the raised taper 40. The distal end 52 of the outer tube 34 is then moved distally until recessed taper 54 mates with raised taper 40 of the core wire 32, whereby further distal movement of the outer tube 34 is limited. Upon mating of the inner core wire 32 and the outer tube 34, torque applied to the outer tube 34 is transmitted to the core wire 32 so that the distal portion 38 of the core wire 32 can be further maneuvered as desired within the vascular system.

In a second additional step, the second over-the-wire catheter is moved distally over the distal end 52 of the outer tube 34 and the distal portion 38 of the inner core wire 32 to a desired position within the vascular system (i.e., balloon is centered in the stenosis). Once the balloon of the second over-the-wire catheter is positioned across the stenosis, the balloon is inflated to open the stenosis and re-establish an acceptable level of blood flow through the arterial vessel.

Figure 6:
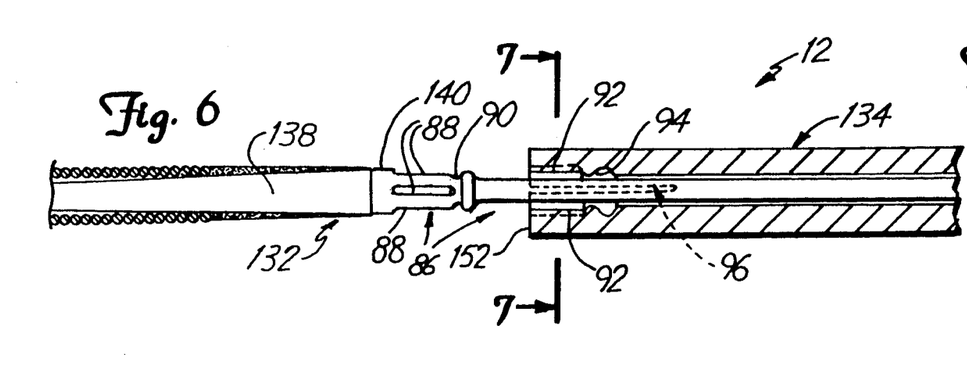
FIG. 6 is an enlarged fragmentary view partially in section of the guide wire assembly of the present invention showing an alternative arrangement for releasably coupling the outer tube to the inner core wire.
Figure 7:
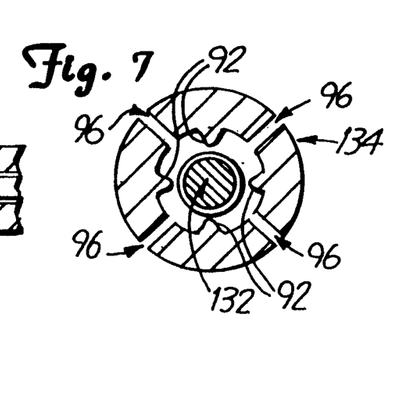
FIG. 7 is a sectional view of the alternative coupling arrangement of the guide wire assembly of the present invention taken along line 7—7 of FIG. 6.

An alternative arrangement is shown in FIGS. 6 and 7 for releasably coupling a distal end 152 of an outer tube 134 to a distal portion 138 of an inner core wire 132. In this embodiment an interference snap fit coupler 86 releasably couples the outer tube 134 to the core wire 132 for torque transmission therebetween. The snap fit coupler 86 includes a plurality of recessed splined grooves 88 formed in a torque transmission portion 140 of the inner core wire 132. A concentric channel 90 is formed in the inner core wire 132 proximally of the grooves 88. A distal end 152 of the outer tube 134 includes mating ribs 92 (see FIG. 7) which are configured to engage the grooves 88 of the inner core wire 132. A concentric ridge 94 is formed on the inner wall 146 of the outer tube 134 and is adapted to engage the concentric channel 90 in a snap fit manner. Between the ribs 92 are longitudinal slots 96 that allow for snap deflection.

The guide wire assembly 12 of the present invention substantially reduces the distal profile of guide wire shafts which allows a reduction in the profile of cooperating exchangeable over-the-wire dilatation catheters 10. The guide wire assembly 12 also does not suffer a loss of control or torqueability that normally occurs when reducing the proximal profile of a typical guide wire to achieve the advantage of use of an exchangeable lower profile catheter. Furthermore, this reduction in catheter profile allows stenoses having smaller openings to be crossed than were previously traversable with the typical larger diameter guide wires. Thus, a greater range of sizes of stenosed arteries can be crossed by over-the-wire dilatation catheters using the guide assembly 12 of the present invention. In addition, the guide wire assembly 12 allows catheters to be exchanged without sacrificing the previously established path through the vascular system to the stenosed area.

Although the present invention has been described with reference to preferred embodiments, workers skilled in the art will recognize that changes may be made in form and detail without departing from the spirit and scope of the invention.

What is claimed is:

1. A guide wire comprising:
 an inner core wire having a proximal end, a distal end and a torque transmission portion therebetween;
 an outer tube having a proximal end and a distal end, the outer tube being coaxially mountable over the proximal end of the inner core wire and movable distally on the inner core wire to the torque transmission portion thereon, such that the proximal end of the outer tube is disposed distally of the proximal end of the inner core wire; and
 means for releasably coupling the distal end of the outer tube to the torque transmission portion of the inner core wire for torque transmission therebetween.

2. The guide wire of claim 1 wherein the inner core wire has a constant diameter between its proximal end and the torque transmission portion.

3. The guide wire of claim 2 wherein the torque transmission portion has a diameter that increases distally to a maximum diameter of the inner core wire.

4. The guide wire of claim 3 wherein the inner core wire has a distal portion between the torque transmission portion and the distal end that has a diameter which decreases distally from the maximum diameter to the distal end.

5. The guide wire of claim 4 wherein the distal portion of the inner core wire has a length approximately ten percent of the inner core wire total length.

6. The guide wire of claim 1 wherein the inner core wire is approximately 300 cm. in length.

7. The guide wire of claim 1 wherein the outer tube has a length at least approximately one-third the length of the inner core wire.

8. The guide wire of claim 1 wherein the outer tube has a constant inner diameter from its proximal end to a point just proximal its distal end.

9. The guide wire of claim 8 wherein the inner diameter of the outer tube increases distally from a point just proximal of its distal end.

10. The guide wire of claim 1 wherein the means for releasably coupling includes:
 a raised taper defined by the inner core wire torque transmission portion; and
 a recessed taper defined by the distal end of outer tube which mates with the raised taper to releasably secure the outer tube to the inner core wire.

11. The guide wire of claim 10 wherein the mating of the raised taper and the recessed taper is by frictional engagement.

12. The guide wire of claim 1 wherein the means for releasably coupling includes:
 a plurality of grooves in one of the torque transmission portion of the inner core wire and an inner wall of the outer tube; and
 a plurality of ribs on the other one of the torque transmission portion and the inner wall, the ribs being configured to engage the grooves such that torque applied to the outer tube will be transmitted to the inner core wire through the interengagement of the ribs and grooves.

13. The guide wire of claim 12 wherein the means for releasably coupling further includes:
 a concentric channel in one of the torque transmission portion and the inner wall; and
 a concentric ridge on the other one of the torque transmission portion and the inner wall, the ridge being adapted to engage the groove in a snap-fit manner when the ribs are engaged with the grooves to releasably secure the outer tube to the inner core wire.

14. The guide wire of claim 13 wherein the plurality of grooves and the concentric channel are in the torque transmission portion of the inner core wire and wherein the plurality of ribs and the concentric ridge are on the inner wall of the outer tube.

15. The guide wire of claim 14 wherein the means for releasably coupling further includes:
 a plurality of longitudinal slots arranged between adjacent ribs, the slots allowing snap deflection of the distal end of the outer tube to permit engagement of the ridge with the channel.

16. The guide wire of claim and further comprising:
 a radiopaque spring tip affixed on the distal end of the inner core wire.

17. The guide wire of claim 16 and further including a safety ribbon extending between and connecting the spring tip and the inner core wire.

18. The guide wire of claim 1 and further including a radiopaque spring tip positioned upon the distal end of the inner core wire, the spring tip including first and second spring coil segments.

19. The guide wire of claim and further including a torque sleeve mounted on the proximal end of the outer tube.

20. The guide wire of claim 1 wherein the inner core wire has a lubricous coating.

21. The guide wire of claim 20 wherein the coating is a polytetrafluoroethylene coating.

22. The guide wire of claim 1 wherein the outer tube has a lubricous coating on an inner wall surface thereof.

23. The guide wire of claim 22 wherein the coating is a silicone coating.

24. The guide wire of claim 1 wherein the outer tube has a lubricous coating on an outer wall surface thereof.

25. The guide wire of claim 24 wherein the coating is a polytetrafluoroethylene coating.

26. A guide wire assembly comprising:
an inner core wire having a proximal end and a distal end, wherein a diameter thereof is constant from the proximal end to a point between the proximal end and the distal end, where the diameter first increases distally to a maximum, forming a taper, then decreases distally to the distal end; and
an outer tube having a proximal end, a distal end and a lumen extending therethrough from the proximal end to the distal end, with the distal end being coaxially mountable over the proximal end of the inner core wire and the distal end having a tapered recess therein which releasably mates with the taper within a vascular system of a patient for coupling the inner core wire and outer tube for torque transmission therebetween, and wherein the proximal end of the outer tube is disposed distally of the proximal end of the inner core wire, thereby providing means for coupling and uncoupling the inner core wire and outer tube with force applied outside the vascular system of the patient.

27. A method for exchanging a first over-the-wire catheter in a vascular system for a second over-the-wire catheter, therein, the method comprising the steps of:
providing a guide wire assembly over which a first over-the-wire catheter is mounted in a vascular system, with the guide wire assembly having an inner wire and an outer tube coaxially movably mounted over the inner wire;
holding a proximal portion of the inner wire outside of the vascular system to maintain the position of the inner wire within the vascular system;
moving the outer tube and the first over-the-wire catheter proximally over the inner wire;
withdrawing the outer tube and the first over-the-wire catheter out of the vascular system to expose a portion of the inner wire distally from a distal end of the first catheter;
holding the inner wire at said exposed portion to hereafter maintain the position of the inner wire within the vascular system;
releasing the proximal portion of the inner wire;
withdrawing the first over-the-wire catheter and the outer tube from the proximal end of the inner wire;
removing the outer tube from within the first over-the-wire catheter;
installing a distal end of the outer tube within the proximal end of a second over-the-wire catheter;
installing the distal end of the outer tube and the second over-the-wire catheter thereon onto the proximal end of the inner wire;
moving the outer tube and second over-the-wire catheter thereon distally over the inner wire to said exposed portion;
holding the proximal portion of the inner wire to maintain the position of the inner wire within the vascular system;
releasing said exposed portion of the inner wire; and
moving the outer tube and second over-the-wire catheter thereon distally over the inner wire to establish the second over-the-wire catheter in a desired position in the vascular system.

28. The method of claim 27, and further comprising the steps of:
advancing the outer tube and second over-the-wire catheter distally over the inner wire to a point where the outer tube and the inner wire mate for torque transmission and further distal advancement of the outer tube is limited; and
moving the second over-the-wire catheter distally over the outer tube and inner wire to a desired position in the vascular system.

* * * * *

UNITED STATES PATENT AND TRADEMARK OFFICE
CERTIFICATE OF CORRECTION

PATENT NO. : 5,246,009

DATED : September 21, 1993

INVENTOR(S) : DANIEL O. ADAMS

It is certified that error appears in the above-identified patent and that said Letters Patent is hereby corrected as shown below:

On the Title Page of the Patent, in the References Cited Section, under U.S. PATENT DOCUMENTS, insert the following:

4,548,206  10/1985  Osborne...........128/772

4,779,628  10/1988  Machek............128/772

4,827,941  5/1989  Taylor et al......128/657

4,846,193  7/1989  Tremulis et al....128/772

4,895,168  1/1990  Machek............128/772

Col. 12, line 60, delete "claim", insert --claim 1--

Col. 13, line 3, delete "claim", insert --claim 1--

Signed and Sealed this

Twenty-ninth Day of March, 1994

Attest:

BRUCE LEHMAN

*Attesting Officer*    *Commissioner of Patents and Trademarks*